US007745495B2

(12) United States Patent
Wendeborn et al.

(10) Patent No.: US 7,745,495 B2
(45) Date of Patent: Jun. 29, 2010

(54) PYRIDINE KETONES WITH HERBICIDAL EFFECT

(75) Inventors: Sebastian Volker Wendeborn, Basel (CH); Renaud Beaudegnies, Basel (CH); Andrew Edmunds, Basel (CH); Christoph Luthy, Basel (CH); Jurgen Schaetzer, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 539 days.

(21) Appl. No.: 11/722,366

(22) PCT Filed: Dec. 20, 2005

(86) PCT No.: PCT/EP2005/013707

§ 371 (c)(1), (2), (4) Date: Jun. 21, 2007

(87) PCT Pub. No.: WO2006/066871

PCT Pub. Date: Jun. 29, 2006

(65) Prior Publication Data

US 2009/0197767 A1 Aug. 6, 2009

(30) Foreign Application Priority Data

Dec. 22, 2004 (GB) ................................ 0428137.4

(51) Int. Cl.

| | |
|---|---|
| ***A01N 35/00*** | (2006.01) |
| ***A01N 25/00*** | (2006.01) |
| ***A01N 43/40*** | (2006.01) |
| ***C07D 211/00*** | (2006.01) |
| ***A01N 33/18*** | (2006.01) |
| ***C07D 211/78*** | (2006.01) |
| ***A61K 31/435*** | (2006.01) |
| ***A61K 33/24*** | (2006.01) |

(52) U.S. Cl. ...................... 514/685; 424/405; 504/244; 514/277; 514/676; 546/315; 546/318

(58) Field of Classification Search ...................... None
See application file for complete search history.

(56) References Cited

FOREIGN PATENT DOCUMENTS

| | | |
|---|---|---|
| GB | 0428137.4 | * 12/2004 |
| WO | 0015615 | 3/2000 |
| WO | 0194339 | 12/2001 |
| WO | 2004058712 | 7/2004 |

OTHER PUBLICATIONS

Youssif ARKIVOC 2001 (i) 242-268.*

* cited by examiner

*Primary Examiner*—Ernst V Arnold
(74) *Attorney, Agent, or Firm*—William A. Teoli, II

(57) ABSTRACT

The invention relates to compounds of formula (I) wherein $A_1$ is $C(R_1R_2)_p$; $A_2$ is $C(R_6R_7)_q$; p is 1 or 2; q is 1 or 2; each of $R_1$, $R_2$, $R_3$, $R_4$, $R_5$, $R_6$, $R_7$ and $R_8$ which may be the same or different, represents hydrogen, methyl or ethyl and $R_9$ is $C_1$-$C_4$alkyl; $R_{10}$ is hydrogen, halogen, $C_1$-$C_3$alkyl or $C_1$-$C_3$-haloalkyl, and agronomically acceptable salts/isomers/enantiomers/tautomers/N-oxides of those compounds.

(I)

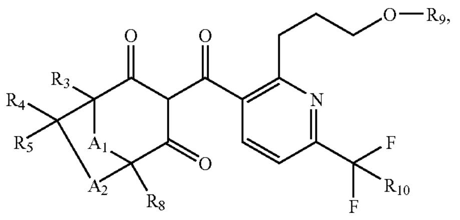

5 Claims, No Drawings

PYRIDINE KETONES WITH HERBICIDAL EFFECT

This application is a 371 of International Application No. PCT/EP2005/013707 filed Dec. 20, 2005, which claims priority to GB 0428137.4 filed Dec. 22, 2004, the contents of which are incorporated herein by reference.

The present invention relates to novel, herbicidally effective pyridine ketones, to compositions comprising said compounds, and to the use thereof for controlling weeds, in particular in crops of cultivated plants or for inhibiting plant growth.

Pyridine ketones with a herbicidal effect are described for example in WO 00/15615. The active ingredients disclosed therein, however, cannot always satisfy requirements with regard to potency and spectrum of action. There is thus a need for active ingredients with improved herbicidal characteristics. It has now been found that pyridine ketones with a specific substitution pattern possess outstanding herbicidal characteristics.

Accordingly, the invention relates to compounds of formula I (I)

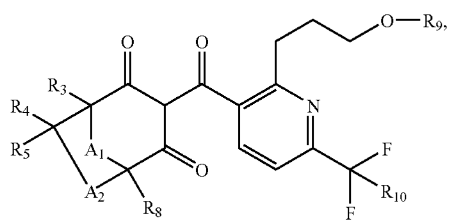

wherein $A_1$ is $C(R_1R_2)_p$;

$A_2$ is $C(R_6R_7)_q$;

p is 1 or 2;

q is 1 or 2;

each of $R_1$, $R_2$, $R_3$, $R_4$, $R_5$, $R_6$, $R_7$ and $R_8$ which may be the same or different, represents hydrogen, methyl or ethyl;

$R_9$ is $C_1$-$C_4$alkyl; and $R_{10}$ is hydrogen, halogen, $C_1$-$C_3$ alkyl or $C_1$-$C_3$-haloalkyl, and agronomically acceptable salts/isomers/enantiomers/tautomers/N-oxides of those compounds.

The alkyl groups occurring in the definitions of the substituents can be straight-chain or branched and are, for example, methyl, ethyl, n-propyl, isopropyl, n-butyl, sec-butyl, iso-butyl or tert-butyl. Halogen as in haloalkyl is fluorine, chlorine, bromine or jodine, preferably fluorine or chlorine.

The invention also embraces the salts which can be formed by the compounds of the formula I, preferably with amines, alkali metal and alkaline earth metal bases or quaternary ammonium bases. Among the alkali metal and alkaline earth metal bases, the hydroxides of lithium, sodium, potassium, magnesium or calcium, in particular those of sodium or potassium, may be especially emphasized as salt formers. Examples of amines suitable for ammonium salt formation are both ammonia and primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o,m,p-toluidines, phenylenediamines, naphthylamines and o,m,p-chloroanilines; but in particular triethylamine, isopropylamine and diisopropylamine. Quaternary ammonium bases which are suitable for salt formation are, for example, $[N(R_{a01}R_{b01}R_{c01}R_{d01})]^+OH^-$, where $R_{a01}$, $R_{b01}$, $R_{c01}$ and $R_{d01}$ independently of one another are $C_1$-$C_4$alkyl. Further suitable tetraalkylammonium bases with other anions can be obtained, for example, by anion exchange reactions.

Preferably p and/or q are 1. Special mention should be made of compounds of formula I wherein $A_1$ and $A_2$ are methylene, $R_1$, $R_2$, $R_6$, $R_7$ and $R_8$ are hydrogen, and $R_3$, $R_4$, $R_5$ independently of each other are hydrogen or methyl, especially hydrogen. Special emphasis should also be given to compounds of formula I, wherein $R_9$ is methyl. Preferred are also compounds where $R_{10}$ is hydrogen, fluorine, chlorine or methyl, especially hydrogen or fluorine. The compounds 3-[6-difluoromethyl-2-(3-methoxy-propyl)-pyridine-3-carbonyl]-bicyclo[3.2.1]octane-2,4-dione and 3-[6-trifluoromethyl-2-(3-methoxy-propyl)-pyridine-3-carbonyl]-bicyclo[3.2.1]octane-2,4-dione are especially preferred.

The compounds of the formula I can be prepared by processes known per se, for example those described in WO 00/15615, for example in the case of compounds of the formula I (I)

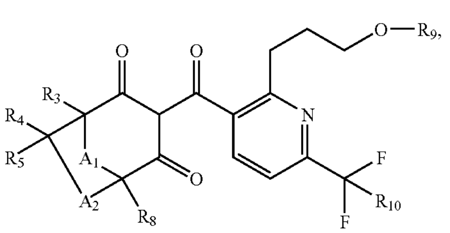

in which $A_1$, $A_2$, $R_3$, $R_4$, $R_5$, $R_8$, $R_9$, and $R_{10}$ are as defined under formula I in claim 1 by (I), a) reacting a compound of the formula IIa (IIa)

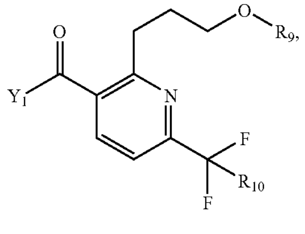

in which $R_9$ and $R_{10}$ are as defined under formula I and $Y_1$ is a leaving group, for example fluorine, chlorine, bromine or cyano, in an inert organic solvent in the presence of a base with a compound of the formula III (III)

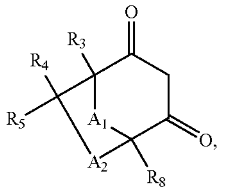

in which $A_1$, $A_2$, $R_3$, $R_4$, $R_5$ and $R_8$ are as defined under formula I, to give the compounds of the formulae IVa and IVb IVa

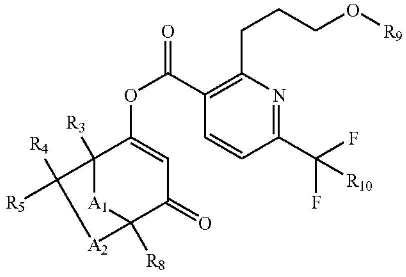

IVb

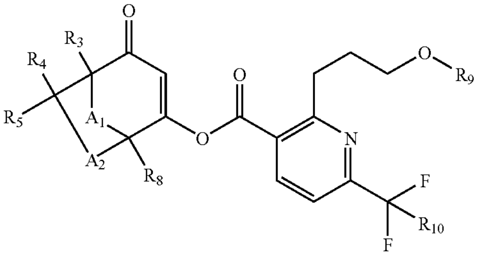

and then isomerizing these for example in the presence of a base and a catalytic amount of dimethylaminopyridine (DMAP) or a source of cyanide, for example acetone cyanohydrin; or b) reacting a compound of the formula IIb (IIb)

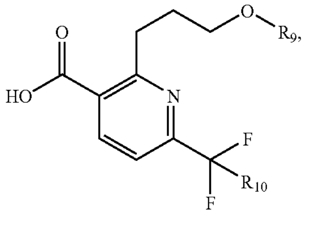

in which $R_9$ and $R_{10}$ are as defined under formula I, with a compound of the formula III (III)

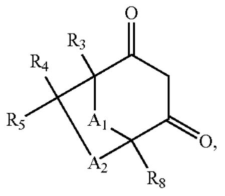

in which $A_1$, $A_2$, $R_3$, $R_4$, $R_5$ and $R_8$ are as defined under formula I in an inert organic solvent in the presence of a base and a coupling agent, for example dicyclohexylcarbodiimide, to give the compounds of the formula IVa or IVb IVa

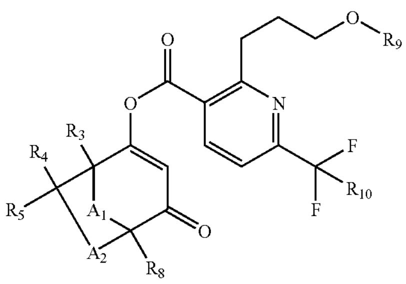

IVb

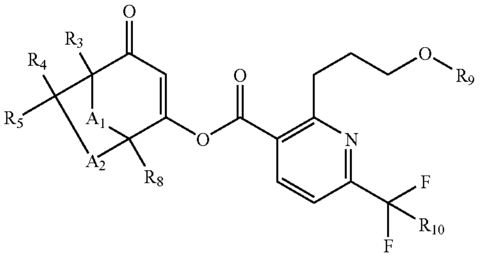

The intermediates of the formulae IIa, IIb, IVa and IVb are novel and are developed specifically for the preparation of the compounds of the formula I. Accordingly, they also form part of the subject matter of the present invention. Together, the novel intermediates of the formulae IIa, IIb, IVa and IVb correspond to formula Va (Va)

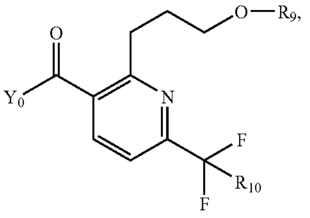

in which $Y_0$ is hydroxyl, fluorine, chlorine, bromine or cyano, or $Y_0$ is a group of the formula $Y_2$ or $Y_3$:

($Y_2$)

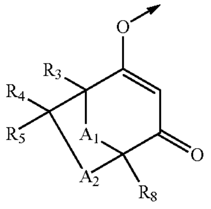

-continued (Y3)

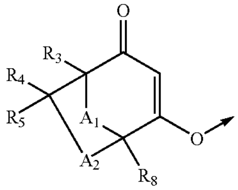

wherein $A_1$, $A_2$, $R_3$, $R_4$, $R_5$, $R_8$, $R_9$ and $R_{10}$ are as defined under formula I and the arrows represent the point of attachment to the carbonyl group of Va.

The preparation of the compounds of the formula I is illustrated in more detail in reaction schemes 1 and 2 below.

Reaction scheme 1

Route a):

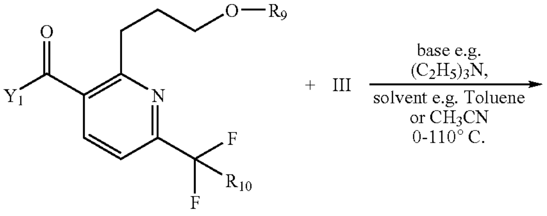

IIa

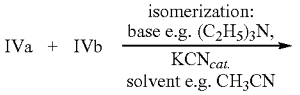

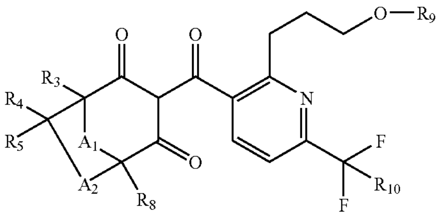

I

Route b):

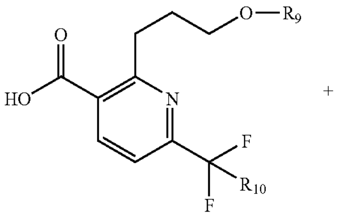

IIb

-continued

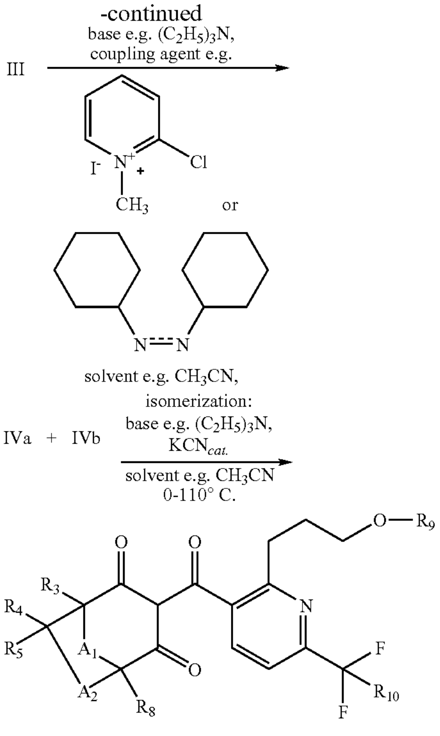

I

According to reaction scheme 1, route a), the carboxylic acid derivatives of the formula IIa in which $Y_1$ is a leaving group such as halogen, for example fluorine, bromine, and in particular chlorine, N-oxyphthalimide or N,O-dimethylhydroxylamino or part of an activated ester, for example

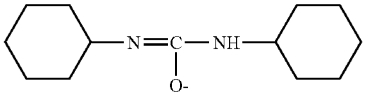

(formed from dicyclohexylcarbodiimide (DCC) and the corresponding carboxylic acid) or

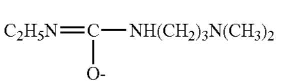

(formed from N-ethyl N'-(3-dimethylaminopropyl)carbodiimide (EDC) and the corresponding carboxylic acid) are used as starting materials for preparing the compounds of the formula I. The starting materials are reacted in an inert organic solvent such as a halogenated hydrocarbon, for example dichloromethane, a nitrile, for example acetonitrile, or an aromatic hydrocarbon, for example toluene, and in the presence of a base such as an alkylamine, for example triethylamine, an aromatic amine, for example pyridine, methylethylpyridine, or 4-dimethylaminopyridine (DMAP) with the dione derivatives of the formula III, to give the isomeric enol esthers of the formula IVa and/or IVb. This esterification can be carried out at temperatures of from 0° C. to 110° C., in particular between 5° C. to 45° C.

The isomerisation of the ester derivatives of the formulae IVa and IVb to derivatives of the formula I can be carried out, for example, similarly to EP-A-0 353 187, EP-A-0 316 491 or WO 00/15615 in the presence of a base such as an alkylamine, for example triethylamine, a carbonate, for example potassium carbonate, and a catalytic amount of DMAP or a source of cyanide, such as acetone cyanohydrin or potassium cyanide. In particular if a cyanide compound of the formula Ia ($Y_1$=cyano) is used, or in the presence of a catalytic amount of acetone cyanohydrin or potassium cyanide, the two reaction steps can be carried out in situ without isolating the intermediates IVa and/or IVb.

According to reaction scheme 1, route b), the desired derivatives of the formula I can be obtained, for example, similarly to E. Haslem, *Tetrahedron,* 2409-2433, 36, 1980, by esterifying the carboxylic acids of the formula IIb with the dione derivatives of the formula III in an inert solvent such as a halogenated hydrocarbon, for example dichloromethane, a nitrile, for example acetonitrile, or an aromatic hydrocarbon, for example toluene, in the presence of a base such as an alkylamine, for example triethylamine, and a coupling agent such as 2-chloro-1-methylpyridinium iodide. Depending on the solvent used, this esterification is carried out at temperatures of from 0° C. to 110° C., giving initially, as described under route a), the isomeric ester of the formula IVa and/or IVb, which can be isomerized as described under route a), for example in the presence of a base and a catalytic amount of DMAP, or a source of cyanide, for example acetone cyanohydrin, to give the desired derivative of the formula I. The activated carboxylic acid derivatives of the formula IIa in reaction scheme 1 (route a), in which $Y_1$ is a leaving group such as halogen, for example bromine, iodine or, in particular, chlorine, can be prepared by known standard processes, for example those described in C. Ferri "Reaktionen der organischen Synthese" [Reactions of Organic Synthesis], Georg Thieme Verlag, Stuttgart, 1978, page 460 ff. Such reactions are generally known and described in the literature in different variations with respect to the leaving group $Y_1$.

Compounds of formula IIb can be manufactured by alkaline hydrolysis of the corresponding $C_1$-$C_6$-alkyl esters IIc

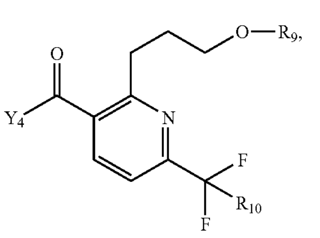

(IIc)

wherein $Y_4$ is $C_1$-$C_6$-alkoxy, allyloxy or benzyloxy, and $R_9$ and $R_{10}$ are as defined under formula I, fusing an alkaline earth metal base, for example LiOH, NaOH or KOH, in a protic solvent, for example $H_2O$ or $H_2O$/methanol mixtures, followed by isolation processes known to the person skilled in the art. A method of manufacture of the $C_1$-$C_6$-alkyl esters of IIc is described in WO 04/078729. Compounds of the formula IIb wherein $R_{10}$ is hydrogen can be prepared from the corresponding compounds of formula IIb, wherein $R_{10}$ is chlorine or bromine, by hydrogen reduction at pressures between 1 and 50 atmospheres in the presence of an appropriate metal catalyst, for example, palladium supported on carbon, in an inert solvent such as methanol, toluene or ethylacetate. Alternatively the $C_1$-$C_6$-alkyl esters of the formula IIc as well as compounds of formula I, wherein $R_{10}$ is chlorine or bromine, can be reduced by hydrogen first at pressures between 1 and 50 atmospheres in the presence of a metal catalyst, for example palladium supported on carbon, in an inert solvent such as methanol, toluene or ethylacetate, and then transformed to the corresponding acid by hydrolysis procedures known to the person skilled in the art. This is illustrated in more detail in scheme 3.

Scheme 3:

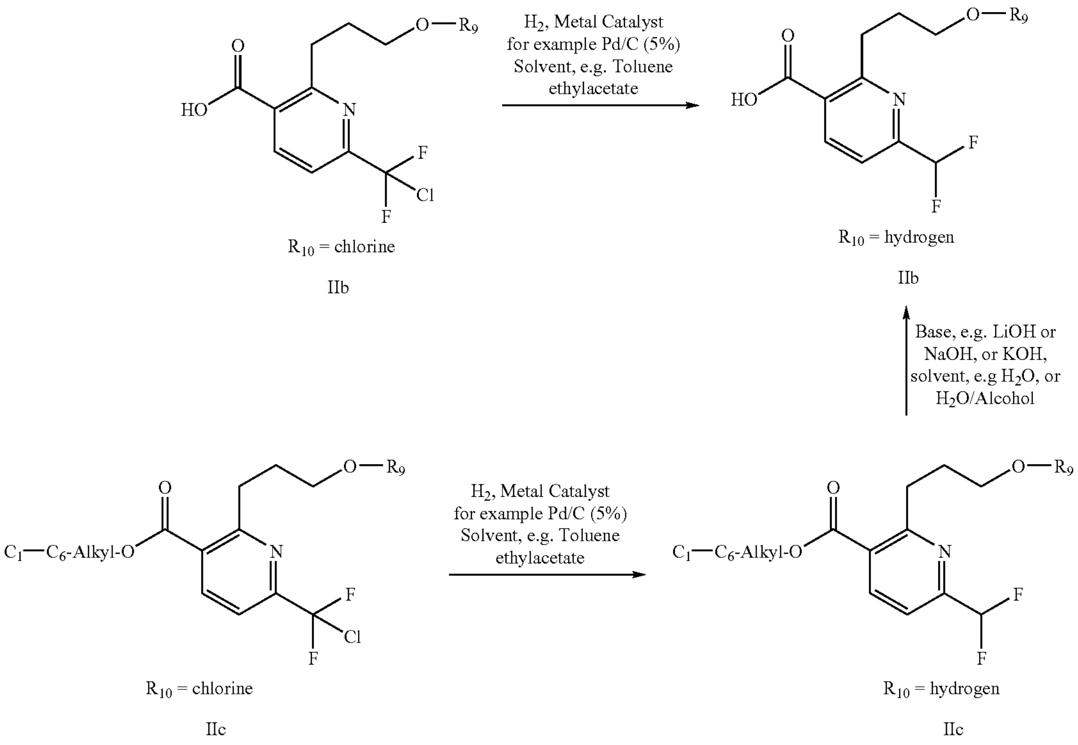

Compounds of Formula IIb and IIc can also be manufactured by reduction of compounds of formula VIa (VIa)

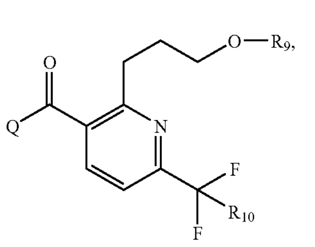

or formula VIb (VIb)

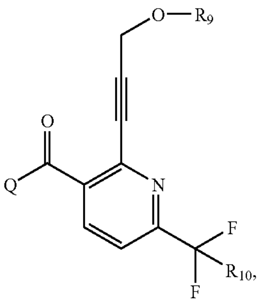

wherein Q is hydroxy, $C_1$-$C_8$-alkoxy, allyloxy or benzyloxy, or a radical of the formula III, (IIIa)

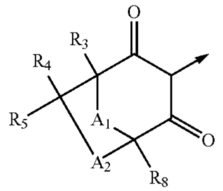

wherein $A_1$, $A_2$, $R_3$, $R_4$, $R_5$, $R_8$, $R_9$ and $R_{10}$ are as defined under formula I, by using hydrogen at pressures between 1 and 50 atmospheres in the presence of an appropriate metal catalyst, for example, palladium supported on carbon, in an inert solvent such as methanol, toluene or ethylacetate. Such reactions are well-known to the person skilled in the art. This is illustrated in more detail in scheme 4.

Scheme 4:

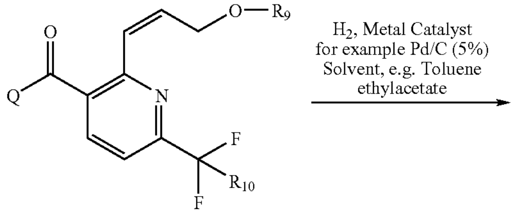

VIa

-continued

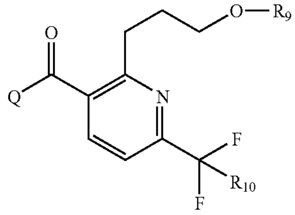

IIc, IIb resp. I

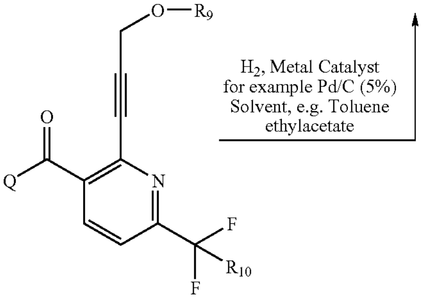

VIb

The compounds of the formula VI are known and can be prepared as described in WO 00/39094 and WO 01/94339.

The compounds of the formula III are known and can be prepared as described, for example, in WO 00/15615 or EP-A-1352890.

For the use according to the invention of the compounds of formula I, or of compositions comprising them, there come into consideration all methods of application customary in agriculture, for example pre-emergence application, post-emergence application and seed dressing, and also various methods and techniques such as, for example, the controlled release of active ingredient. For that purpose a solution of the active ingredient is applied to mineral granule carriers or polymerized granules (urea/formaldehyde) and dried. If required, it is additionally possible to apply a coating (coated granules), which allows the active ingredient to be released in metered amounts over a specific period of time.

The invention therefore relates also to a herbicidal and plant-growth-inhibiting composition comprising a herbicidal effective amount of a compound of formula I according to claim 1 on an inert carrier.

The compounds of formula I can be used as herbicides in unmodified form, that is to say as obtained in the synthesis, but they are preferably formulated in customary manner together with the adjuvants conventionally employed in formulation technology e.g. into emulsifiable concentrates, directly sprayable or dilutable solutions, dilute emulsions, suspensions, mixtures of a suspension and an emulsion (suspoemulsions), wettable powders, soluble powders, dusts, granules or microcapsules. Such formulations are described, for example, on pages 9 to 13 of WO 97/34485. As with the nature of the compositions, the methods of application, such as spraying, atomising, dusting, wetting, scattering or pouring, are selected in accordance with the intended objectives and the prevailing circumstances.

The formulations, that is to say the compositions, preparations or mixtures comprising the compound (active ingredient) of formula I or at least one compound of formula I and, usually, one or more solid or liquid formulation adjuvants, are prepared in known manner, e.g. by homogeneously mixing and/or grinding the active ingredients with the formulation adjuvants, for example solvents or solid carriers. Surface-active compounds (surfactants) may also be used in addition in the preparation of the formulations. Examples of solvents and solid carriers are given, for example, on page 6 of WO 97/34485.

Depending upon the nature of the compound of formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, on pages 7 and 8 of WO 97/34485.

In addition, the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna 1981, and M. and J. Ash, "Encyclopedia of Surfactants", Vol. I-III, Chemical Publishing Co., New York, 1980-81, are also suitable for the preparation of the herbicidal compositions according to the invention.

The compositions according to the invention can additionally include an additive comprising an oil of vegetable or animal origin, a mineral oil, alkyl esters thereof or mixtures of such oils and oil derivatives.

The amount of oil additive in the composition according to the invention is generally from 0.01 to 2%, based on the spray mixture. For example, the oil additive can be added to the spray tank in the desired concentration after the spray mixture has been prepared.

Preferred oil additives comprise mineral oils or an oil of vegetable origin, for example rapeseed oil, olive oil or sunflower oil, emulsified vegetable oil, such as AMIGO® obtainable from Rhône-Poulenc Canada Inc., alkyl esters of oils of vegetable origin, for example the methyl derivatives, or an oil of animal origin, such as fish oil or beef tallow. A preferred additive contains as active components essentially 80% by weight alkyl esters of fish oils and 15% by weight methylated rapeseed oil, and also 5% by weight of customary emulsifiers and pH modifiers.

Especially preferred oil additives comprise alkyl esters of higher fatty acids ($C_8$-$C_{22}$), especially the methyl derivatives of $C_{12}$-$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Henkel subsidiary Cognis GMBH, DE).

The application and action of the oil additives can be improved by combining them with surface-active substances, such as non-ionic, anionic or cationic surfactants. Examples of suitable anionic, non-ionic and cationic surfactants are listed on pages 7 and 8 of WO 97/34485.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available, preferred surfactants are the Genapol types (Clariant AG, Muttenz, Switzerland). Also preferred for use as surface-active substances are silicone surfactants, especially polyalkyl-oxide-modified heptamethyltrisiloxanes, such as are commercially available as e.g. Silwet L-77®, and also perfluorinated surfactants. The concentration of surface-active substances in relation to the total additive is generally from 1 to 30% by weight.

Examples of oil additives that consist of mixtures of oils or mineral oils or derivatives thereof with surfactants are Edenor ME SU®, Turbocharge® (Zeneca Agro, Stoney Creek, Ontario, Calif.) and Actipron® (BP Oil UK Limited, GB).

The addition of an organic solvent to the oil additive/surfactant mixture can also bring about a further enhancement of action. Suitable solvents are, for example, Solvesso® (ESSO) and Aromatic Solvent® (Exxon Corporation) types. The concentration of such solvents can be from 10 to 80% by weight of the total weight.

Such oil additives, which are also described, for example, in U.S. Pat. No. 4,834,908, are suitable for the composition according to the invention. A commercially available oil additive is known by the name MERGE®, is obtainable from the BASF Corporation and is essentially described, for example, in U.S. Pat. No. 4,834,908 in col. 5, as Example COC-1. A further oil additive that is preferred according to the invention is SCORE® (Novartis Crop Protection Canada.)

In addition to the oil additives listed above, in order to enhance the action of the compositions according to the invention it is also possible for formulations of alkyl pyrrolidones, such as are commercially available e.g. as Agrimax®, to be added to the spray mixture. Formulations of synthetic latices, such as, for example, polyacrylamide, polyvinyl compounds or poly-1-p-menthene, such as are commercially available as e.g. Bond®, Courier® or Emerald®, can also be used to enhance action. Solutions that contain propionic acid, for example Eurogkem Pen-e-trate®, can also be added as action-enhancing agent to the spray mixture.

The herbicidal formulations generally contain from 0.1 to 99% by weight, especially from 0.1 to 95% by weight, of herbicide, from 1 to 99.9% by weight, especially from 5 to 99.8% by weight, of a solid or liquid formulation adjuvant, and from 0 to 25% by weight, especially from 0.1 to 25% by weight, of a surfactant. Whereas commercial products will preferably be formulated as concentrates, the end user will normally employ dilute formulations. The compositions may also comprise further ingredients, such as stabilisers, for example vegetable oils or epoxidised vegetable oils (epoxidised coconut oil, rapeseed oil or soybean oil), anti-foams, for example silicone oil, preservatives, viscosity regulators, binders, tackifiers, and also fertilisers or other active ingredients.

The compounds of formula I are generally applied to the plant or to the locus thereof at rates of application of from 0.001 to 4 kg/ha, especially from 0.005 to 2 kg/ha. The concentration required to achieve the desired effect can be determined by experiment. It is dependent upon the nature of the action, the stage of development of the cultivated plant and of the weed and on the application (place, time, method) and may vary within wide limits as a function of those parameters.

The compounds of formula I are distinguished by herbicidal and growth-inhibiting properties, allowing them to be used in crops of useful plants, especially cereals, cotton, soybeans, sugar beet, sugar cane, plantation crops, rape, maize and rice, and also for non-selective weed control.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate mmonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a CryIIIB (b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from

*Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Other indication areas for the active ingredients of the invention are the protection of stored products and stores and of material and, in the hygiene sector, especially the protection of domestic animals and livestock against pests of said type.

The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica.*

The compositions according to the invention may additionally comprise growth regulators, for example trinexapac (744), chlormequat chloride (129), clofencet (148), cyclanilide (170), ethephon (281), flurprimidol (355), gibberellic acid (379), inabenfide (421), maleic hydrazide (449), mefluidide (463), mepiquat chloride (465), paclobutrazol (548), prohexadione-calcium (595), uniconazole (746) or thidiazuron (703). It is also possible for a composition according to the invention to comprise fungicides, for example azoxystrobin (43), epoxiconazole (48), benomyl (60), bromuconazole (89), bitertanol (77), carbendazim (107), cyproconazole (189), cyprodinil (190), diclomezine (220), difenoconazole (228), diniconazole (247), epoxiconazole (48), ethirimol (284), etridiazole (294), fenarimol (300), fenbuconazole (302), fenpiclonil (311), fenpropidin (313), fenpropimorph (314), ferimzone (321), fludioxonil (334), fluquinconazole (349), flutolanil (360), flutriafol (361), imazalil (410), ipconazole (426), iprodione (428), isoprothiolane (432), kasugamycin (438), kresoxim-methyl (439), spiroxamine (441), mepronil (466), myclobutanil (505), nuarimol (528), pefurazoate (554), pencycuron (556), phthalide (576), probenazole (590), prochloraz (591), propiconazole (607), pyrazophos (619), pyroquilone (633), quinoxyfen (638), quintozene (639), tebuconazole (678), tetraconazole (695), thiabendazole (701), thifluzamide (705), triadimefon (720), triadimenol (721), tricyclazole (734), tridemorph (736), triflumizole (738), triforine (742), triticonazole (745) or vinclozolin (751). The number in brackets after each active ingredient refers to the entry number of that active ingredient in the Pesticide Manual, eleventh ed., British Crop Protection Council, 1997.

The following examples further illustrate, but do not limit the invention.

EXAMPLE 1

Preparation of 3-[6-Difluoromethyl-2-(3-Methoxy-Propyl)-Pyridine-3-Carbonyl]-Bicyclo [3.2.1]Octane-2,4-Dione (H-3)

A solution of 194 g of 6-(Chloro-difluoro-methyl)-2-(3-methoxy-propyl)-nicotinic acid methyl ester (prepared according to WO 04/078729) in methanol (ca. 2 liter) and triethylamine (100 ml) is hydrogenated at 1 Atm hydrogen pressure in the presence of 2 g of 5% palladium supported on carbon. After completion of the reduction the reaction mixture is filtered through hyflo, and the filtrate diluted with water and the water/methanol mixture then extracted with ethyl acetate. The combined ethyl acetate extracts are washed with saturated aqueous sodium chloride solution, dried over magnesium sulphate and then concentrated in vacuo to give 194.2 g 6-Difluoromethyl-2-(3-methoxy-propyl)-nicotinic acid methyl ester as a pale coloured oil.

A solution of 181 g of 6-Difluoromethyl-2-(3-methoxy-propyl)-nicotinic acid methyl ester in 750 ml of a 2:1 methanol/water mixture is treated with 43.9 g of lithium-hydroxide monohydrate, and the mixture stirred at ambient temperature for 1 hour. Then the methanol is removed by distillation in vacuo, and the reaction mixture then diluted with crushed ice and acidified with aqueous 6N hydrochloric acid. The product is filtered and washed thoroughly with water. Crystallisation from n-hexane:methylene chloride gives 138.3 g of 6-Difluoromethyl-2-(3-methoxy-propyl)-nicotinic acid as white crystals (melting point 86-87° C.). A solution of 101.2 g of 6-Difluoromethyl-2-(3-methoxy-propyl)-nicotinic acid in 1250 ml of dichloromethane is charged initially, 1 ml of dimethylformamide are added and the mixture is subsequently treated with 38.4 ml of oxalyl chloride. After the intensive evolution of gas has ceased, the mixture is stirred at room temperature for 1 hour and then cooled to 0° C. and treated with 57 g of bicyclo[3.2.1]octane-2,4-dione and 87 ml of triethylamine and the mixture then stirred for 2 hours at ambient temperature. The mixture is then diluted with methylene chloride, and washed with cold 1N hydrochloric acid, dried over magnesium sulphate and concentrated in vacuo to give 150.9 g of 6-Difluoromethyl-2-(3-methoxy-propyl)-nicotinic acid 4-oxo-bicyclo[3.2.1]oct-2-en-2-yl ester as an oil which is used in the next step without further purification.

Under an atmosphere of nitrogen and with stirring 150.9 g of 6-Difluoromethyl-2-(3-methoxy-propyl)-nicotinic acid 4-oxo-bicyclo[3.2.1]oct-2-en-2-yl ester is dissolved in 1500 ml of acetonitrile at 25° C., and the mixture is treated with 86.3 ml of triethylamine and 3.8 ml of acetone cyanohydrin and stirred at room temperature for 20 hours. then concentrated in vacuo. The syrup that remains is chromatographed on silica gel. The viscous oil obtained by eluting with a mixture of toluene, ethyl alcohol, dioxane, triethylamine and water (100:40:20:20:5 parts by volume) is dissolved in ethyl acetate and washed successively with 10% hydrochloric acid and water. The organic solution is dried over $Na_2SO_4$ and concentrated, giving 123.4 g of the title compound 3-[6-Difluoromethyl-2-(3-methoxy-propyl)-pyridine-3-carbonyl]-bicyclo[3.2.1]octane-2,4-dione in the form of a viscous oil. A sample recrystallised from diethyl ether/hexane has a melting point of 45-46° C.

Preferred compounds of formula I and their intermediates of formula Vb are listed in Tables 1 and 2. In the following tables, the free bonds represent methyl groups.

TABLE 1
Compounds of formula I:
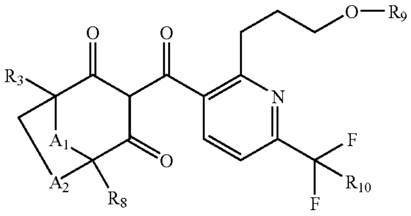
(I)
| Comp. No. | $R_{10}$ | $R_9$ | $R_3$ | $R_8$ | $A_1$ | $A_2$ | Phys. data | Structure |
|---|---|---|---|---|---|---|---|---|
| H-1 | H | $CH_3$ | $CH_3$ | H | $CH_2$ | $CH_2$ | wax | 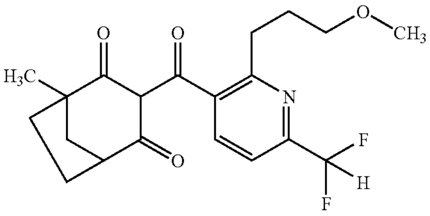 |
| H-2 | H | $CH_3$ | $CH_3$ | $CH_3$ | $CH_2$ | $CH_2$ | | 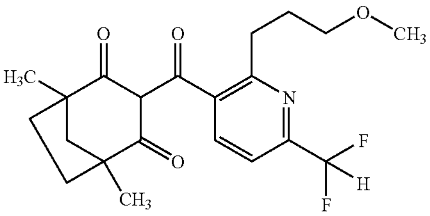 |
| H-3 | H | $CH_3$ | H | H | $CH_2$ | $CH_2$ | 45-46° C. | 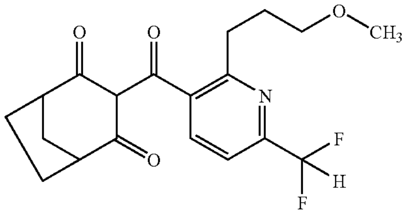 |
| H-4 | H | $CH_3$ | H | H | $CH_2CH_2$ | $CH_2$ | gum | 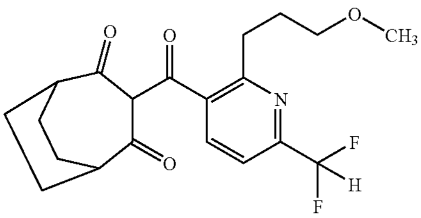 |
| H-7 | H | $CH_3CH_2$ | H | H | $CH_2$ | $CH_2$ | | 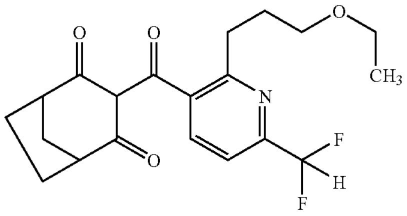 |

TABLE 1-continued
Compounds of formula I:
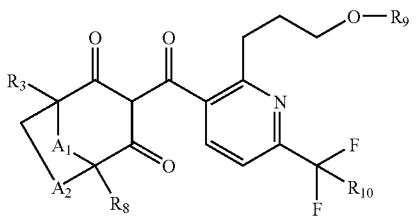
(I)
| Comp. No. | $R_{10}$ | $R_9$ | $R_3$ | $R_8$ | $A_1$ | $A_2$ | Phys. data | Structure |
|---|---|---|---|---|---|---|---|---|
| H-8 | Cl | $CH_3CH_2$ | H | H | $CH_2$ | $CH_2$ | | 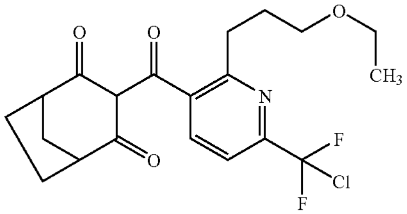 |
| H-9 | Cl | $CH_3$ | H | H | $CH_2$ | $CH_2$ | gum | 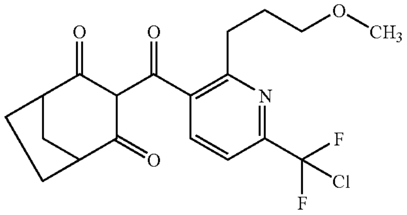 |
| H-10 | Cl | $CH_3$ | H | H | $CH_2CH_2$ | $CH_2$ | | 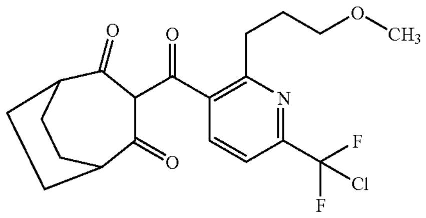 |
| H-11 | $CH_3$ | $CH_3$ | H | H | $CH_2$ | $CH_2$ | | 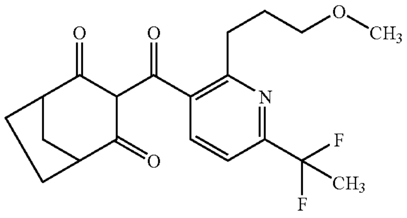 |
| H-12 | $CH_3CH_2$ | $CH_3$ | H | H | $CH_2$ | $CH_2$ | | 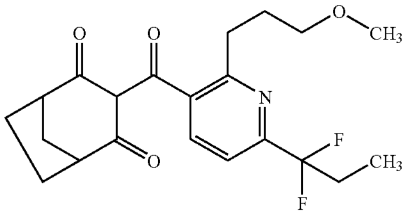 |

TABLE 1-continued
Compounds of formula I:
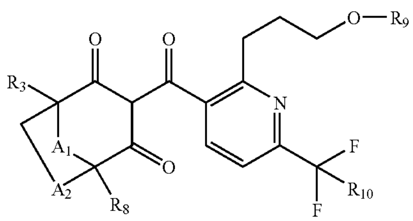
(I)
| Comp. No. | $R_{10}$ | $R_9$ | $R_3$ | $R_8$ | $A_1$ | $A_2$ | Phys. data | Structure |
|---|---|---|---|---|---|---|---|---|
| H-13 | $CF_3$ | $CH_3$ | H | H | $CH_2$ | $CH_2$ | | 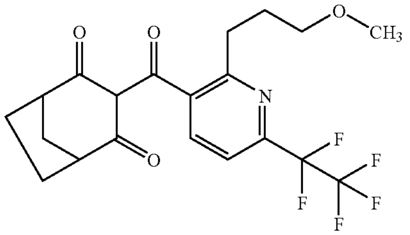 |
| H-14 | F | $CH_3$ | H | H | $CH_2$ | $CH_2$ | wax | 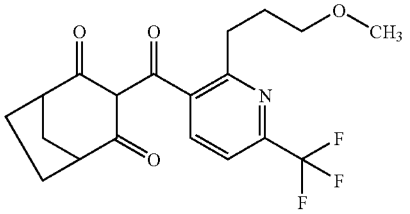 |
| H-15 | F | $CH_xCH_3$ | H | H | $CH_2$ | $CH_2$ | wax | 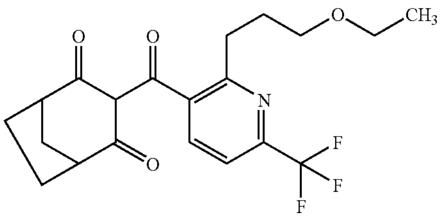 |
| H-16 | F | $CH_3$ | H | $CH_3$ | $CH_2$ | $CH_2$ | wax | 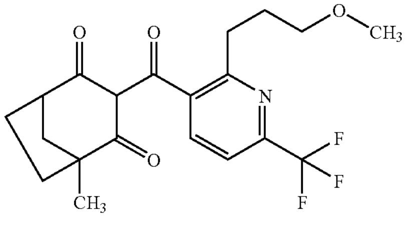 |
| H-17 | F | $CH_3$ | H | $CH_2CH_3$ | $CH_2$ | $CH_2$ | wax | 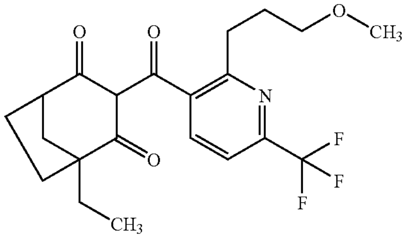 |

TABLE 1-continued
Compounds of formula I:
(I)
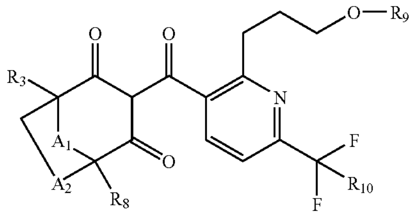
| Comp. No. | $R_{10}$ | $R_9$ | $R_3$ | $R_8$ | $A_1$ | $A_2$ | Phys. data | Structure |
|---|---|---|---|---|---|---|---|---|
| H-18 | F | $CH_3$ | H | H | $CH_2CH_2$ | $CH_2$ | | 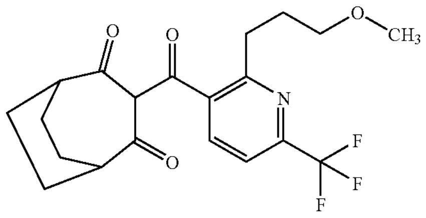 |
| H-19 | F | $CH_3$ | H | H | $CH_2$ | $CH_2CH_2$ | gum | 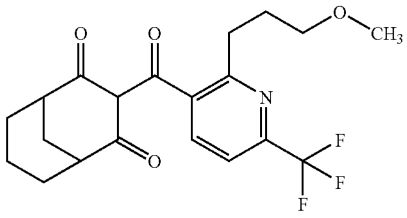 |
| H-20 | Cl | $CH_3$ | H | H | $CH_2$ | $CH_2CH_2$ | | 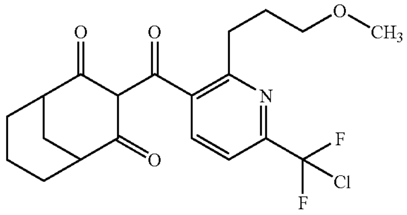 |
| H-21 | H | $CH_3$ | H | H | $CH_2$ | $CH_2CH_2$ | gum | 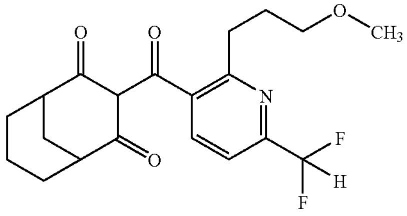 |

TABLE 2
Compounds of formula Vb:
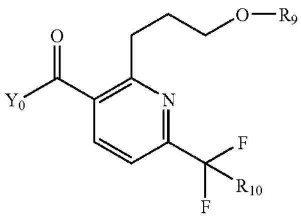
(Vb)
| Comp. No. | $R_{10}$ | $R_9$ | $Y_0$ | phys. data | Structure |
|---|---|---|---|---|---|
| I-1 | F | $CH_3$ | OH | solid | 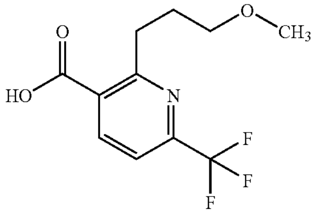 |
| I-2 | Cl | $CH_3$ | OH | solid | 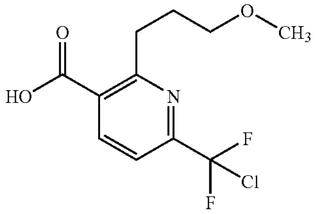 |
| I-3 | H | $CH_3$ | OH | solid | 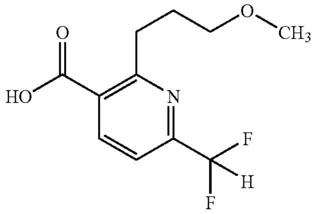 |
| I-4 | F | $CH_3$ | OH | wax | 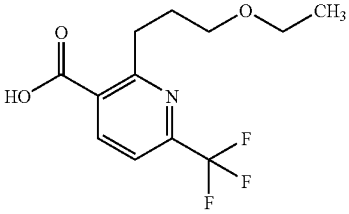 |
| I-5 | F | $CH_3$ | OH | | 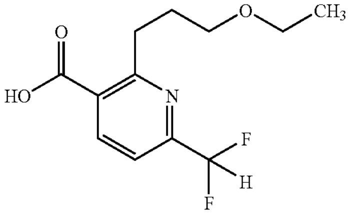 |

TABLE 2-continued

Compounds of formula Vb:

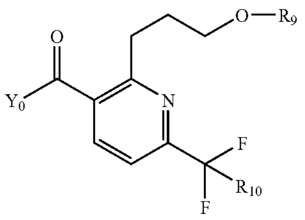

(Vb)

| Comp. No. | $R_{10}$ | $R_9$ | $Y_0$ | phys. data | Structure |
|---|---|---|---|---|---|
| I-6 | F | $CH_3$ | OH | | 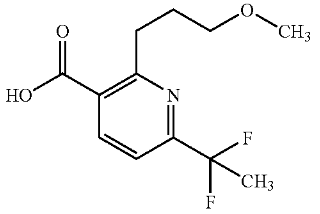 |
| I-7 | F | $CH_3$ | OH | | 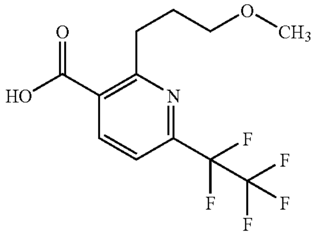 |

BIOLOGICAL EXAMPLES

Example B1

Herbicidal Action Prior to Emergence of the Plants (Pre-Emergence Action)

Monocotyledonous and dicotyledonous test plants are sown in standard soil in plastic pots. Immediately after sowing, the test compounds, in the form of an aqueous suspension (prepared from a 25% wettable powder (Example F3, b) according to WO 97/34485) or in the form of an emulsion (prepared from a 25% emulsifiable concentrate (Example F1, c)), are applied by spraying a concentration corresponding to 125 g or 250 g of active ingredient/ha (500 liter of water/ha). The test plants are then grown in a greenhouse under optimum conditions. After a test duration of 3 weeks, the test is evaluated in accordance with a scale of ten ratings (10=total damage, 0=no action). Ratings of from 10 to 7 (especially from 10 to 8) indicate good to very good herbicidal action. The compounds of formula I exhibit strong herbicidal action in this test. Examples of the good herbicidal action of the compounds are given in Table B1:

TABLE B1

Pre-emergence herbicidal action:

| Ex. No. | g/ha | *Panicum* | *Digitaria* | *Echinochloa* | *Abutilon* | *Amaranthus* | *Chenopodium* | *Stellaria* |
|---|---|---|---|---|---|---|---|---|
| H-1 | 250 | 9 | 9 | 9 | 9 | 9 | 10 | 7 |
| H-3 | 250 | 10 | 10 | 10 | 10 | 10 | 10 | 8 |
| H-4 | 250 | 9 | 9 | 9 | 9 | 9 | 9 | 7 |
| H-9 | 250 | 10 | 10 | 10 | 10 | 9 | 9 | 7 |
| H-14 | 250 | 10 | 10 | 10 | 10 | 10 | 10 | 8 |
| H-15 | 250 | 10 | 9 | 10 | 10 | 10 | 10 | 10 |
| H-16 | 250 | 10 | 10 | 10 | 10 | 8 | 9 | 8 |
| H-21 | 250 | 10 | 10 | 9 | 7 | 7 | 10 | 10 |

Example B2

Post-Emergence Herbicidal Action

In a greenhouse, monocotyledonous and dicotyledonous test plants are grown in standard soil in plastic pots and at the 4- to 6-leaf stage are sprayed with an aqueous suspension of the test compounds of formula I prepared from a 25% wettable powder (Example F3, b) according to WO 97/34485) or with an emulsion of the test compounds of formula I prepared from a 25% emulsifiable concentrate (Example F1, c) according to WO 97/34485), in a concentration corresponding to 125 g or 250 g of active ingredient/ha (500 liter of water/ha). The test plants are then grown on in a greenhouse under optimum conditions. After a test duration of about 18 days, the test is evaluated in accordance with a scale of ten ratings (10=total damage, 0=no action). Ratings of from 10 to 7 (especially from 10 to 8) indicate good to very good herbicidal action. The compounds of formula I exhibit a strong herbicidal action in this test. Examples of the good herbicidal action of the compounds are given in Table B2:

TABLE B2

| | | Post-emergence herbicidal action: | | | | | | | |
|---|---|---|---|---|---|---|---|---|---|
| Ex. No. | g/ha | *Setaria* | *Panicum* | *Digitaria* | *Abutilon* | *Ipomea* | *Chenopodium* | *Sinapis* | *Stellaria* |
| H-1 | 250 | 8 | 9 | 9 | 9 | 9 | 8 | 8 | 8 |
| H-3 | 250 | 9 | 10 | 9 | 9 | 8 | 10 | 9 | 9 |
| H-4 | 250 | 7 | 9 | 9 | 8 | 7 | 7 | 9 | 8 |
| H-9 | 250 | 9 | 9 | 9 | 9 | 9 | 9 | 7 | 8 |
| H-14 | 250 | 10 | 10 | 9 | 10 | 10 | 10 | 10 | 10 |
| H-15 | 250 | 8 | 9 | 8 | 9 | 8 | 10 | 9 | 9 |
| H-16 | 250 | 10 | 10 | 9 | 9 | 9 | 10 | 10 | 10 |
| H-17 | 250 | 8 | 8 | 7 | 9 | 7 | 8 | 9 | 9 |
| H-19 | 250 | 8 | 8 | 9 | 8 | 8 | 9 | 9 | 8 |
| H-21 | 250 | 8 | 9 | 9 | 8 | 8 | 9 | 9 | 8 |

Comparative Example 1

Comparison of the Biological Activity of the Compounds According to the Invention with Compounds According to the Prior Art In the following Table B3, the pre-emergent herbicidal activity of compound H-14 according to the invention is compared with 4 compounds according to the prior art. All compounds are structurally identical except for the nature of the alkylene linker attached to the pyridine ring.

TABLE B3

| | | Pre-emergent Herbicidal Activity: | | | | | | |
|---|---|---|---|---|---|---|---|---|
| Comp. No. | g/ha | Corn | Soya | *Setaria* | *Echinochloa* | *Brachiaria* | *Abutilon* | *Amaranthus* |
| H-14 | 30 | 0 | 3 | 10 | 10 | 8 | 10 | 7 |
| | 15 | 0 | 1 | 9 | 9 | 7 | 9 | 7 |
| A | 30 | 0 | 5 | 7 | 9 | 7 | 9 | 7 |
| | 15 | 0 | 2 | 6 | 4 | 6 | 9 | 7 |
| B | 30 | 1 | 8 | 9 | 10 | 9 | 9 | 8 |
| | 15 | 1 | 6 | 8 | 9 | 6 | 8 | 6 |
| C | 30 | 0 | 0 | 2 | 3 | 0 | 4 | 5 |
| | 15 | 0 | 0 | 2 | 3 | 0 | 3 | 3 |
| F | 30 | 0 | 0 | 6 | 7 | 6 | 8 | 7 |
| | 15 | 0 | 0 | 3 | 4 | 0 | 8 | 7 |

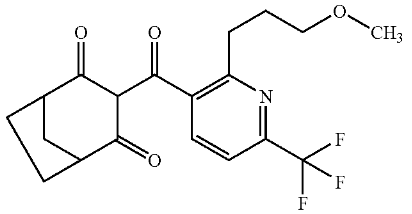

H-14

TABLE B3-continued

| Pre-emergent Herbicidal Activity: | | | | | | | | |
|---|---|---|---|---|---|---|---|---|
| Comp. No. | g/ha | Corn | Soya | *Setaria* | *Echinochloa* | *Brachiaria* | *Abutilon* | *Amaranthus* |
| 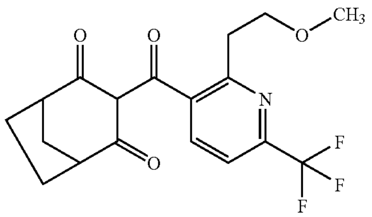 A | | | | | | | | |
| 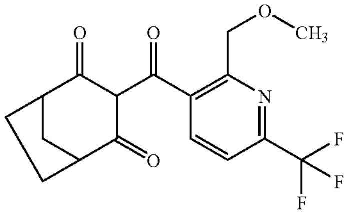 B | | | | | | | | |
| 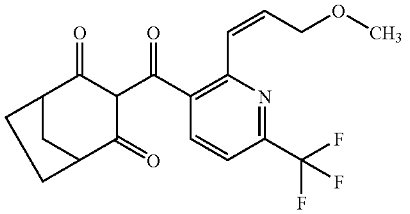 C | | | | | | | | |
| 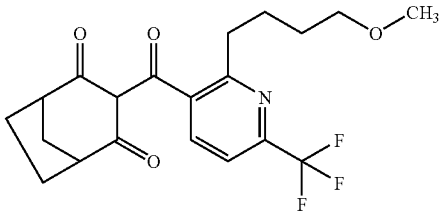 F | | | | | | | | |

Results:

As is evident from the data in Table B3, compound H-14 according to the present invention shows at the same application rates a significantly improved herbicidal activity against monocotyledon weeds, and an improved selectivity against culture plants such as corn, and especially soya, than compound A, (example 1.023 Table 1, WO 00/15615), compound B (example 1.021 Table 1, WO 00/15615), and compound C (example A364-B52, WO 01/94339). Compound F has been prepared in order to demonstrate the effect of an extension of the alkylene linker from propylene (instant invention) to butylene. Compound F shows no phytotoxic effect on the crop plants, but its herbicidal action is significantly lower when compared with compound H-14 according to the instant invention. Especially an application rate of 15 g/ha, compound F shows very weak herbicidal action against *Setaria* and *Echinochloa*. These results are indicative of the superior selective herbicidal activity of the inventive compounds. This enhanced effect was not to be expected on the basis of the structural similarity of these compounds.

Comparative Example 2

Comparison of the Biological Activity of the Compounds According to the Invention with Compounds According to the Prior Art In the following Table B4, the pre-emergent herbicidal activity of compound H-3 according to the invention is compared with compound D according to the prior art. Both compounds are structurally identical except for the length of the alkylene linker attached to the pyridine ring.

TABLE B4

| Pre-emergent Herbicidal Activity: | | | | | | | | | |
|---|---|---|---|---|---|---|---|---|---|
| Comp. No. | g/ha | Corn | Soya | *Panicum* | *Digitaria* | *Echinochloa* | *Abutilon* | *Xanthium* | *Amaranthus* |
| H-3 | 60 | 0 | 0 | 10 | 9 | 10 | 10 | 7 | 10 |
| | 30 | 0 | 0 | 10 | 9 | 10 | 9 | 7 | 9 |
| D | 60 | 0 | 3 | 9 | 9 | 7 | 9 | 0 | 7 |
| | 30 | 0 | 2 | 8 | 7 | 5 | 6 | 0 | 7 |

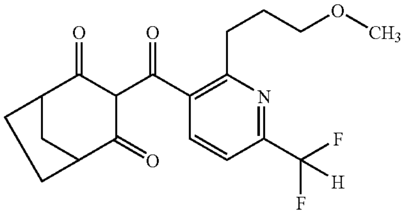

H-3

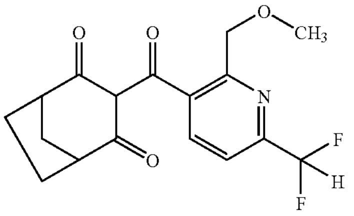

D

Results:

In Table B4, the pre-emergent herbicidal activity of the compound H-3 shows at the same application rates an improved activity against monocotyledon and dicotyledon weeds, together with improved selectivity against culture plants such as corn, and especially soya, when compared with compound D (Example 1.302 Table 1, WO 00/15615). This enhanced effect was not to be expected on the basis of the structural similarity of these compounds.

Comparative Example 3

Comparison of the Biological Activity of the Compounds According to the Invention with Compounds According to the Prior Art In the following Table B5, the pre-emergent herbicidal activity of compound H-9 according to the invention is compared with compound E according to the prior art. Both compounds are structurally identical except for the length of the alkylene linker attached to the pyridine ring.

TABLE B5

| Pre-emergent Herbicidal Activity: | | | | | | | | | |
|---|---|---|---|---|---|---|---|---|---|
| Comp. No. | g/ha | *Mais* | *Soja* | *Digitaria* | *Echinochloa* | *Brachiaria* | *Scirpus* | *Abutilon* | *Amaranthus* |
| H-9 | 60 | 1 | 1 | 9 | 10 | 9 | 10 | 9 | 8 |
| | 30 | 0 | 0 | 8 | 9 | 9 | 10 | 8 | 8 |

TABLE B5-continued

| Pre-emergent Herbicidal Activity: | | | | | | | | | |
|---|---|---|---|---|---|---|---|---|---|
| Comp. No. | g/ha | *Mais* | *Soja* | *Digitaria* | *Echinochloa* | *Brachiaria* | *Scirpus* | *Abutilon* | *Amaranthus* |
| E | 60 | 0 | 4 | 6 | 9 | 0 | 9 | 0 | 7 |
| | 30 | 0 | 2 | 6 | 8 | 0 | 9 | 0 | 5 |

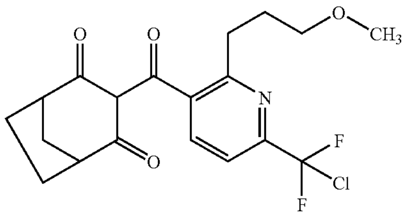

H-9

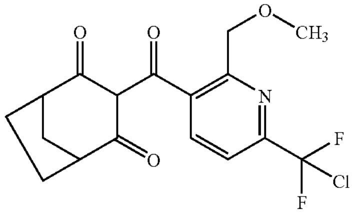

E

Results:

In Table B5, the pre-emergent herbicidal activity of the compound H-9 shows at the same application rates an improved activity against monocotyledon and dicotyledon weeds, together with improved selectivity against culture plants such as corn, and especially soya, when compared with compound E (Example 1.240 Table 1, WO 00/15615). Under consideration of the structural similarities of both compounds, the superior biological activity of compound H-9 according to the present invention is completely unexpected.

What is claimed is:

1. A compound of formula I (I)

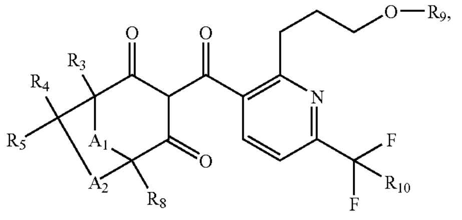

wherein $A_1$ is $C(R_1R_2)_p$;

$A_2$ is $C(R_6R_7)_q$;

p is 1 or 2;

q is 1 or 2;

each of $R_1$, $R_2$, $R_3$, $R_4$, $R_5$, $R_6$, $R_7$ and $R_8$ which may be the same or different, represents hydrogen, methyl or ethyl;

$R_9$ is $C_1$-$C_4$alkyl; and $R_{10}$ is hydrogen, halogen, $C_1$-$C_3$ alkyl or $C_1$-$C_3$-haloalkyl; and the agronomically acceptable salts/isomers/enantiomers/tautomers/N-oxides of those compounds.

2. A compound of formula Va (Va)

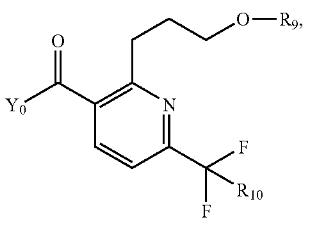

wherein $Y_0$ is hydroxy, fluorine, chlorine, bromine or cyano, or $Y_0$ is a group of the formula $Y_2$ or $Y_3$:

($Y_2$)

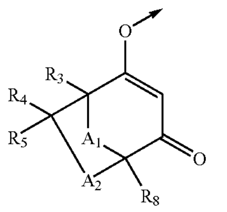

($Y_3$)

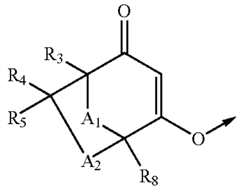

wherein $A_1$, $A_2$, $R_3$, $R_4$, $R_5$ and $R_8$ are defined as in formula I in claim 1;

$R_9$ is $C_1$-$C_4$alkyl; and $R_{10}$ is hydrogen, halogen, $C_1$-$C_3$-alkyl or $C_1$-$C_3$-haloalkyl.

3. A herbicidal and plant-growth-inhibiting composition, comprising a herbicidally effective amount of a compound of formula I according to claim 1 on an inert carrier.

4. A method of controlling undesired plant growth, which method comprises applying a compound of formula I according to claim 1, or a composition comprising such a compound, in a herbicidally effective amount to a plant or to the locus thereof.

5. A method of inhibiting plant growth, which method comprises applying a compound of formula I according to claim 1, or a composition comprising such a compound, in a herbicidally effective amount to a plant or to the locus thereof.

* * * * *